US00PP19663P2

(12) United States Plant Patent
Ogden et al.

(10) Patent No.: US PP19,663 P2
(45) Date of Patent: Jan. 27, 2009

(54) ***OENOTHERA* PLANT NAMED 'SHIMMER'**

(50) Latin Name: *Oenothera fremontii*
Varietal Denomination: Shimmer

(76) Inventors: Scott Ogden, 2455 Stonecrest Dr., Fort Collins, CO (US) 80521; Lauren S. Ogden, 2455 Stonecrest Dr., Fort Collins, CO (US) 80521

( * ) Notice: Subject to any disclaimer, the term of this patent is extended or adjusted under 35 U.S.C. 154(b) by 0 days.

(21) Appl. No.: 11/981,886

(22) Filed: Nov. 2, 2007

(51) Int. Cl.
*A01H 5/00* (2006.01)

(52) U.S. Cl. ..... Plt./460
(58) Field of Classification Search ..... Plt./460
See application file for complete search history.

*Primary Examiner*—Wendy C. Haas

(57) ABSTRACT

A new cultivar of *Oenothera* plant named 'SHIMMER', a hardy deciduous herbaceous perennial, distinguishable by low-spreading habit, narrow silver, ribbon-like foliage, and bright butter-yellow flowers. In combination these traits set 'SHIMMER' apart from all other existing varieties of *Oenothera* known to the inventor.

2 Drawing Sheets

Genus: *OENOTHERA*.
Species: *fremontii*.
Denomination: 'SHIMMER'.

BACKGROUND OF THE INVENTION

The present invention relates to a new and distinct cultivar of evening primrose, a hardy herbaceous perennial grown for use in the landscape. The new invention, known botanically as *Oenothera fremontii* is a member of the Onagraceae family and will hereinafter be referred to by the cultivar name 'SHIMMER'.

The new *Oenothera* cultivar named 'SHIMMER' was discovered in the inventor's experimental garden as a chance seedling that resulted from open pollination. The inventor selected 'SHIMMER' in 2004 as a superior seedling selection based on the criteria of dramatically narrow, ribbon-like foliage, and overall appearance in the garden setting. The selection process was carried out by the inventor in Fort Collins, Colo.

The female parent is *Oenothera fremontii* (unpatented) and the male parent is *Oenothera fremontii* (unpatented). The name *Oenothera fremontii* is known by the inventor to be synonymous with *Oenothera macrocarpa* subsp. *fremontii*. 'SHIMMER' is distinguishable from the parent by foliage and overall appearance.

The closest comparison plant known to the inventor is *Oenothera fremontii* 'Lemon Silver' (unpatented). The new variety named 'SHIMMER' is distinguishable from the comparison plant by dramatically narrow, ribbon-like foliage. When compared to 'Lemon Silver' the foliage of 'SHIMMER' is fine textured, giving a more obviously silver effect, and an overall appearance that is neat and luxuriant. Other related perennials such as *Oenothera* subsp. *incana* 'Comanche Campfire' (unpatented) and 'Silver Blade' (unpatented) present a coarse appearance and require 30% to 40% more garden space when compared to the new *Oenothera* plant named 'SHIMMER'.

The distinguishing characteristics of the new *Oenothera* plant named 'SHIMMER' are low-spreading habit, narrow silver, ribbon-like leaves, red stems, and butter-yellow flowers that are fragrant at night. 'SHIMMER' grows 10 cm. in height and 20 cm. to 25 cm. in width the first year, reaching 15 cm. in height and 60 cm. in width at maturity. The new cultivar named 'SHIMMER' is deciduous, highly drought tolerant, and hardy to USDA Zone 4.

Due to finely branching stems, many flowers appear at the ends of the numerous stems at once, resulting in a floriferous show of bloom during early summer and sporadically through the remainder of the growing season. Unlike other evening primrose, 'SHIMMER' is as beautiful in foliage as in flower, creating a silver carpet, dotted with bright butter-yellow flowers when in bloom.

The first asexual reproduction of 'SHIMMER' was conducted in June 2005, in a cultivated area of Fort Collins, Colo. The method used was softwood cuttings. Since that time 'SHIMMER' has been determined fixed, stable and true to type in subsequent generations of asexual propagation.

SUMMARY OF THE INVENTION

The following traits have been repeatedly observed and represent the distinguishing characteristics of the new *Oenothera* cultivar named 'SHIMMER'. These traits in combination distinguish 'SHIMMER' from all other existing varieties of *Oenothera* known to the inventor. 'SHIMMER' has not been tested under all possible conditions and phenotypic differences may be observed with variations in environmental, climatic, and cultural conditions, however, without any variance in genotype.

1. 'SHIMMER' exhibits low-spreading habit.
2. 'SHIMMER' exhibits narrow silver, ribbon-like leaves.
3. 'SHIMMER' exhibits bright butter-yellow flowers that are fragrant at night.
4. 'SHIMMER' exhibits contrasting red stems.
5. 'SHIMMER' reaches 15 cm. in height and 60 cm. in width at maturity.
6. 'SHIMMER' blooms in early summer and sporadically through the remainder of the growing season.
7. 'SHIMMER' is drought tolerant.
8. 'SHIMMER' is hardy to USDA Zone 4.

BRIEF DESCRIPTION OF THE DRAWINGS

The accompanying color drawings illustrate the overall appearance of the new *Oenothera* cultivar named 'SHIMMER' showing color as true as is reasonably possible to obtain in color reproductions of this type. Color in the drawings may differ from color values cited in the detailed botanical description, which accurately describe the actual color of the new variety 'SHIMMER'. The drawings were made in summer of 3-year-old plants that were planted in the ground from 1-liter containers.

The drawing labeled

The drawing labeled

Figure 1:
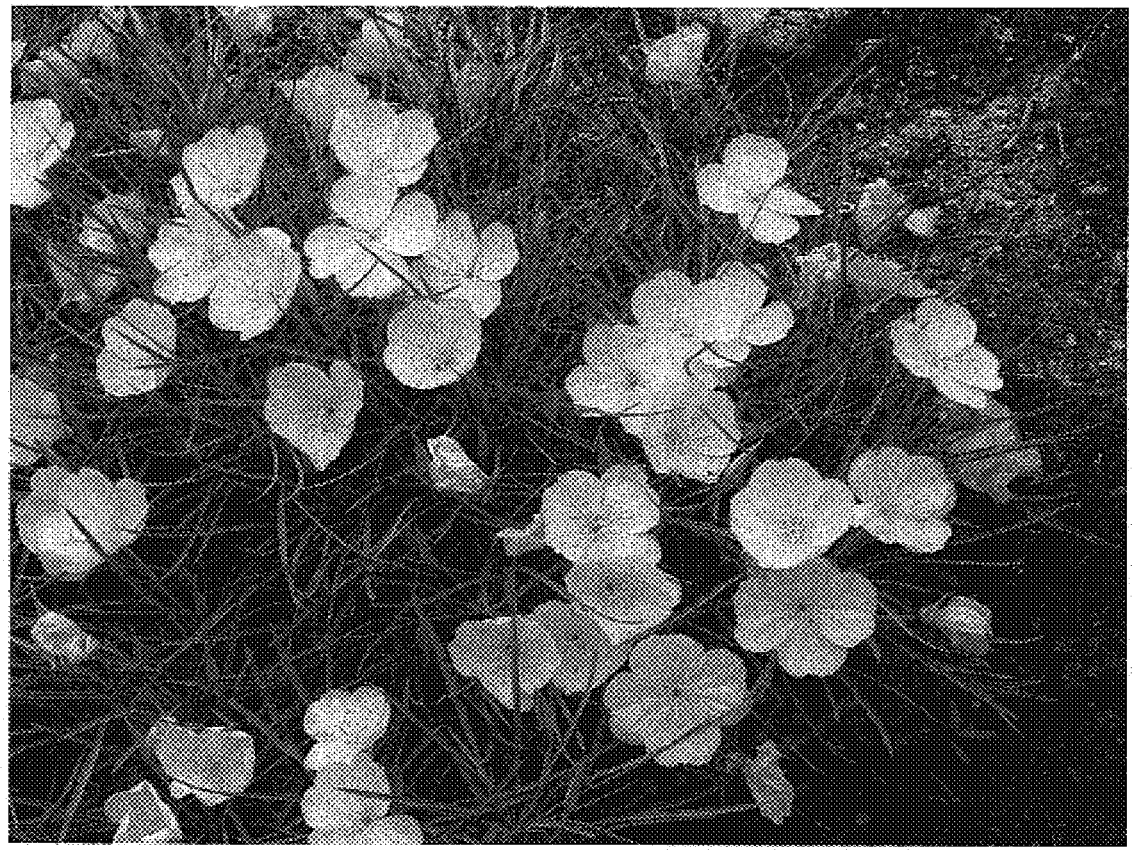
FIG. 1 depicts a plant in bloom illustrating habit and overall appearance.
Figure 2:
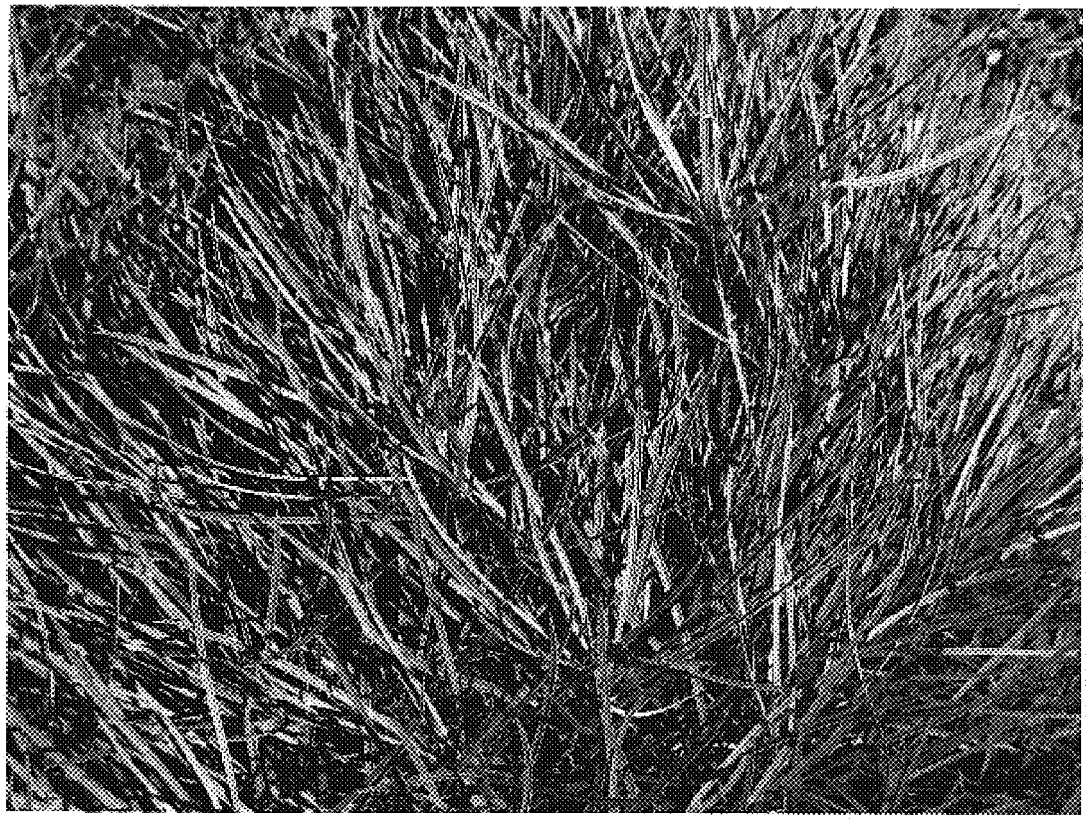
FIG. 2 depicts a close-up view of the foliage.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Oenothera* cultivar named 'SHIMMER'. Observations, measurements, values and comparisons were collected in Arroyo Grande, Calif. during summer from 3-year-old plants grown in 14 cm. containers. Color determinations are made in accordance with The 2001 Royal Horticultural Society Colour Chart from London, England, except where general color terms of ordinary dictionary significance are used.

Botanical classification: *Oenothera fremontii* 'SHIMMER'.
Family: Onagraceae.
Genus: *Oenothera.*
Species: *fremontii.*
Denomination: 'SHIMMER'.
Common name: Evening primrose.
Habit: Low-spreading habit.
Commercial category: Herbaceous perennial.
Use: For use in the landscape.
Suggested commercial container sizes: 14 cm. and 1-liter containers.
Parentage: *Oenothera fremontii* 'SHIMMER' was discovered as a chance seedling resulting from open-pollination of the following parents:
*Female parent.*—*Oenothera fremontii.*
*Male Parent.*—*Oenothera fremontii.*
Propagation method: Softwood cuttings.
Rooting system: Taproot and fibrous roots.
Vigor (range): Low to moderate.
Time to develop roots (range): 15–30 days.
Temperature to develop roots (range): 20–21 Centigrade.
Crop time (range): 4–6 months are needed to produce a 14 cm. container plant from a rooted cutting.
Plant dimensions (first year): 10 cm. in height and 20 cm. to 25 cm. in width.
Plant dimensions (at maturity): 15 cm. in height and 60 cm. in width.
Cultural requirements: Grow in full sun and loam or well-draining soil, with low to moderate water.
Pest or disease resistance: No pest or disease resistance known to the inventor.
Pest or disease susceptibility: No pest or disease susceptibility known to the inventor.
Hardiness: USDA Zone 4.
Other consideration: Highly drought tolerant.

Stem:
*Habit.*—Low-spreading habit.
*Stem color.*—182A.
*Stem length* (*range*).—6–8 cm.
*Stem width.*—0.50 cm.
*Stem shape.*—Cylindrical.
*Stem surface.*—Puberulent.
*Branching.*—Decumbent.
*Internode length* (*range*).—0.10 cm. to 1 cm.

Foliage:
*Type.*—Deciduous.
*Leaf arrangement.*—Combination of alternate and whorled.
*Leaf division.*—Simple.
*Margin.*—Entire.
*Leaf shape.*—Linear and sulcate.
*Leaf length* (*range*).—8 cm. to 10 cm.
*Leaf width.*—0.40 cm.
*Leaf base.*—Truncate.
*Leaf apex.*—Narrow acute.
*Venation.*—Parallel.
*Vein color* (*abaxial and adaxial surfaces*).—191D.
*Leaf surface* (*abaxial*).—Puberulent.
*Leaf surface* (*adaxial*).—Puberulent.
*Leaf attachment.*—Sessile.
*Stipules or spines.*—None observed.
*Leaf color* (*abaxial surface*).—189A.
*Leaf color* (*adaxial surface*).—191D.
*Fragrance.*—None observed.

Inflorescence:
*Inflorescence type.*—Solitary.
*Aspect.*—Facing upward.
*Blooming seasons.*—Early summer and sporadically through fall.
*Peduncle length* (average).—6 cm.
*Peduncle width.*—3 mm.
*Peduncle shape.*—Cylindrical.
*Peduncle surface.*—Puberulent.
*Peduncle color.*—N144A.
*Bud shape.*—Fusiform.
*Bud dimensions.*—3 cm. in length and 0.60 cm. in widths.
*Bud color.*—193A.
*Bud surface.*—Puberulent.
*Bud apex.*—Acute.
*Flower shape.*—Funnel.
*Flower quantity* (*range*).—15–20 per 14 cm. container plant.
*Flower color.*—5A.
*Flower depth.*—3 cm.
*Flower diameter.*—4.50.
*Petal quantity.*—4 in number.
*Petal shape.*—Obdeltoid.
*Petals fused or unfused.*—Unfused.
*Petal apex.*—Emarginate.
*Petal margins.*—Slightly serrate.
*Petal dimensions.*—2.75 cm. in length and 3 cm. in width.
*Petal color* (*abaxial and adaxial surfaces*).—5A.
*Petal surfaces* (*abaxial and adaxial*).—Glabrous and sinuate.
*Calyx shape.*—Reflexed.
*Calyx color.*—N144A.
*Calyx surfaces* (*adaxial and abaxial*).—Glabrous.
*Calyx dimensions.*—1 cm. in height and 1 cm. in width.
*Sepals.*—4 in number.

*Sepal color* (*abaxial and adaxial surfaces*).—N144A.
*Sepal apex.*—Acute.
*Sepal base.*—Truncate.
*Sepal surfaces* (*abaxial and adaxial*).—Glabrous.
*Sepal margin.*—Entire.
*Sepals fused or unfused.*—Apically fused.
*Self-cleaning or persistent.*—Self-cleaning.
*Fragrance of inflorescene.*—Sweet fragrance at night.
*Lastingness of individual flower.*—Ephemeral.

Reproductive organs:
*Stamen quantity.*—8 in number.
*Stamen length.*—2.75 cm.
*Stamen color.*—162A.
*Anther length.*—1.50 cm.
*Anther color.*—162A.
*Anther shape.*—Filiform.
*Pollen quantity.*—Heavy.
*Pollen color.*—162A.
*Pistil quantity.*—1 in number.
*Stigma height.*—4 mm. in height and 2 mm. in width.
*Stigma color.*—162A.
*Stigma shape.*—Retrorse.
*Ovary position.*—Inferior.
*Ovary color.*—189C.
*Ovary shape.*—Terete winged.
*Ovary dimensions.*—1 cm. in height and 0.40 cm. in width.

Fruit: None observed.

What is claimed is:

1. A new and distinct cultivar of *Oenothera* plant named 'SHIMMER' as described and illustrated herein.

* * * * *